US012766187B2

(12) United States Patent
Jost et al.

(10) Patent No.: US 12,766,187 B2
(45) Date of Patent: Oct. 20, 2026

(54) LYMPHOTOXIN ALPHA FOR USE IN THERAPY OF MYELOID LEUKEMIA

(71) Applicant: CYCURIA THERAPEUTICS GMBH, Graz (AT)

(72) Inventors: Philipp J. Jost, Graz (AT); Ulrike Höckendorf, Munich (DE)

(73) Assignee: CYCURIA THERAPEUTICS GMBH, Graz (AT)

( * ) Notice: Subject to any disclaimer, the term of this patent is extended or adjusted under 35 U.S.C. 154(b) by 1215 days.

(21) Appl. No.: 17/608,446

(22) PCT Filed: May 15, 2020

(86) PCT No.: PCT/EP2020/063609
§ 371 (c)(1),
(2) Date: Nov. 2, 2021

(87) PCT Pub. No.: WO2020/229660
PCT Pub. Date: Nov. 19, 2020

(65) Prior Publication Data

US 2022/0193195 A1 Jun. 23, 2022

(30) Foreign Application Priority Data

May 16, 2019 (EP) .................................... 19174964

(51) Int. Cl.

| | |
|---|---|
| ***A61K 38/19*** | (2006.01) |
| ***A61K 31/704*** | (2006.01) |
| ***A61K 31/7068*** | (2006.01) |
| ***A61K 38/05*** | (2006.01) |
| ***A61P 35/02*** | (2006.01) |

(52) U.S. Cl.
CPC .......... *A61K 38/191* (2013.01); *A61K 31/704* (2013.01); *A61K 31/7068* (2013.01); *A61K 38/05* (2013.01); *A61P 35/02* (2018.01)

(58) Field of Classification Search
CPC ................ A61K 38/191; A61K 31/704; A61K 31/7068; A61K 38/05; A61K 38/1841; A61P 35/02
See application file for complete search history.

(56) References Cited

FOREIGN PATENT DOCUMENTS

| | | | | |
|---|---|---|---|---|
| WO | 1966001121 A1 | | 1/1996 | |
| WO | 2010/129789 A2 | | 11/2010 | |
| WO | WO-2016029043 A1 | * | 2/2016 | ......... A61K 38/1793 |

OTHER PUBLICATIONS

Uniprot, TNFB Human (P01374), 2019, pp. 1-8, retrieved from: https://www.uniprot.org/uniprotkb/P01374/publications (Year: 2019).*
Bhattacharya et al., Impact of genetic variation on three dimensional structure and function of proteins, 2017, PLoS One, vol. 12, Issue 3, pp. 1-22 (Year: 2017).*
Fenton et al., Rheostat positions: A new classification of protein positions relevant to pharmacogenomics, 2020, Medicinal Chemistry Research, vol. 29, pp. 1133-1146 (Year: 2020).*
Guo et al., Protein tolerance to random amino acid change, 2004, PNAS, vol. 101, No. 25, pp. 9205-9210 (Year: 2004).*
Wingfield, N-Terminal Methionine Processing, 2018, Current Protocols in Protein Science, vol. 88, pp. 1-4 (Year: 2018).*
USPTO Life Science Example 28, 2016 (Year: 2016).*
Elbaz et al., Tumor Necrosis Factor and Human Acute Leukemia, 1994, Leukemia & Lymphoma, vol. 12, Issue 3-4, pp. 191-195 (Year: 1994).*
Tian et al., TNF-a, a good or bad factor in hematological disease, 2014, Stem Cell Investigation, vol. 1, Issue 12, pp. 1-12 ( Year: 2014).*
Kubota et al., Tumor necrosis factor alpha and lymphotoxin stimulate human myeloblastic leukemia cell (ML-1) invasion through a reconstituted basement membrane (Matrigel) with concomitant induction of 92 kDa gelatinase secretion, 1996, Cancer Letters, vol. 98, pp. 233-240 (Year: 1996).*
Japanese Office Action for JP Application No. 2021-568511 mailed May 7, 2024 (10 pages, English translation).
P.J. Jost et al., “Necroinflammation emerges as a key regulator of hematopoiesis in health and disease” Cell Death and Differentiation, Sep. 21, 2018, vol. 26 No. 1; pp. 53-67.
PCT, “International Search Report & Written Opinion” Application No. PCT/EP2020/063609, mailed Aug. 27, 2020; 15 pages.
Altschul et al. (Nucleic Acids Res. (1997) 25: 3389-3402).
Dohner, H. et al. (2017). Blood 129, 424-447.
Hockendorf, U. et al. (2016) Cancer Cell 30, 75-91.
Jost Philipp J. et al.: “Necroinflammation emerges as a key regulator of hematopoiesis in health and disease”, Cell Death and Differentiation, Nature Publishing Group, GB, vol. 26, No. 1, Sep. 21, 2018, pp. 53.67.
Karlin and Altschul (Proc. Natl. Acad. Sci. USA (1993) 90: 5873-5877).
Peake, K. et al. (2015). J. Vis Exp, e52553.
Shlush, L. I. et al. (2014). Nature 506, 328-333.
Extended European Search Report of EP19174964, dated Nov. 19, 2019, 6 pages.
International Search Report and Written Opinion of PCT/EP2020/063609, mailed Aug. 27, 2020, 5 pages.
International Preliminary Report on Patentability of PCT/EP2020/063609, mailed Nov. 16, 2021, 6 pages.
Altschul et al., “Basic Local Alignment Search Tool,” Journal of Molecular Biology, vol. 215, pp. 403.410, 1990.

* cited by examiner

*Primary Examiner* — Jeffrey Stucker
*Assistant Examiner* — Brittney E Donoghue
(74) *Attorney, Agent, or Firm* — MH2 Technology Law Group, LLP

(57) ABSTRACT

The present invention relates to a polypeptide for use in the treatment of myeloid diseases or myeloid neoplasms, a pharmaceutical composition comprising such a polypeptide for use in the treatment of myeloid diseases or myeloid neoplasms and a kit comprising such a polypeptide for use in the treatment of myeloid diseases or myeloid neoplasms.

16 Claims, 5 Drawing Sheets

Specification includes a Sequence Listing.

```
                       SEQUENCE LISTING


<160> NUMBER OF SEQ ID NOS: 6

<210> SEQ ID NO 1
<211> LENGTH: 205
<212> TYPE: PRT
<213> ORGANISM: Homo sapiens
<220> FEATURE:
<223> OTHER INFORMATION: Full-length Lymphotoxin alpha

<400> SEQUENCE: 1

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205


<210> SEQ ID NO 2
```

```
<211> LENGTH: 172
<212> TYPE: PRT
<213> ORGANISM: Homo sapiens
<220> FEATURE:
<223> OTHER INFORMATION: Mature form of Lymphotoxin alpha (signal
      peptide aa 1 to 34 replaced by an N-terminal Met)

<400> SEQUENCE: 2

Met Leu Pro Gly Val Gly Leu Thr Pro Ser Ala Ala Gln Thr Ala Arg
1               5                   10                  15

Gln His Pro Lys Met His Leu Ala His Ser Thr Leu Lys Pro Ala Ala
            20                  25                  30

His Leu Ile Gly Asp Pro Ser Lys Gln Asn Ser Leu Leu Trp Arg Ala
        35                  40                  45

Asn Thr Asp Arg Ala Phe Leu Gln Asp Gly Phe Ser Leu Ser Asn Asn
    50                  55                  60

Ser Leu Leu Val Pro Thr Ser Gly Ile Tyr Phe Val Tyr Ser Gln Val
65                  70                  75                  80

Val Phe Ser Gly Lys Ala Tyr Ser Pro Lys Ala Thr Ser Ser Pro Leu
                85                  90                  95

Tyr Leu Ala His Glu Val Gln Leu Phe Ser Ser Gln Tyr Pro Phe His
            100                 105                 110

Val Pro Leu Leu Ser Ser Gln Lys Met Val Tyr Pro Gly Leu Gln Glu
        115                 120                 125

Pro Trp Leu His Ser Met Tyr His Gly Ala Ala Phe Gln Leu Thr Gln
    130                 135                 140

Gly Asp Gln Leu Ser Thr His Thr Asp Gly Ile Pro His Leu Val Leu
145                 150                 155                 160

Ser Pro Ser Thr Val Phe Phe Gly Ala Phe Ala Leu
                165                 170


<210> SEQ ID NO 3
<211> LENGTH: 455
<212> TYPE: PRT
<213> ORGANISM: Homo sapiens
<220> FEATURE:
<223> OTHER INFORMATION: Tumor necrosis factor receptor 1

<400> SEQUENCE: 3

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140
```

```
Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455


<210> SEQ ID NO 4
<211> LENGTH: 461
<212> TYPE: PRT
<213> ORGANISM: Homo sapiens
<220> FEATURE:
<223> OTHER INFORMATION: Tumor necrosis factor receptor 2

<400> SEQUENCE: 4

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45
```

-continued

```
Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460
```

<210> SEQ ID NO 5
<211> LENGTH: 435
<212> TYPE: PRT
<213> ORGANISM: Homo sapiens
<220> FEATURE:
<223> OTHER INFORMATION: Tumor necrosis factor receptor superfamily
member 3 = Lymphotoxin beta receptor

<400> SEQUENCE: 5

```
Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
    130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365
```

```
Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
        435


<210> SEQ ID NO 6
<211> LENGTH: 283
<212> TYPE: PRT
<213> ORGANISM: Homo sapiens
<220> FEATURE:
<223> OTHER INFORMATION: Herpes virus entry mediator

<400> SEQUENCE: 6

Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280
```

LYMPHOTOXIN ALPHA FOR USE IN THERAPY OF MYELOID LEUKEMIA

CROSS REFERENCE TO RELATED APPLICATIONS

This application claims the priority benefit of PCT/EP2020/063609 filed on May 15, 2020 which claims the priority benefit to EP patent application Ser. No. 19/174,964.7, filed May 16, 2019, the entire contents of which are incorporated herein by reference.

TECHNICAL FIELD

The present invention relates to a polypeptide comprising the amino acid sequence of the full length human lymphotoxin alpha or the mature form of human lymphotoxin alpha or a sequence having at least 80% identity to one of these amino acid sequences for use in the treatment of myeloid diseases or myeloid neoplasms, a pharmaceutical composition comprising such a polypeptide for use in the treatment of myeloid diseases or myeloid neoplasms and a kit comprising such a polypeptide for use in the treatment of myeloid diseases or myeloid neoplasms.

BACKGROUND OF THE INVENTION

Acute myeloid leukemia (AML) is a heterogeneous disorder characterized by clonal expansion of primitive myeloid lineage cells (blasts) in the bone marrow and peripheral blood, and consequently bone marrow failure. Recent studies have revealed that AML, chronic myeloid leukemia (CML) as well as other myeloid diseases arise from the sequential acquisition of recurrent genetic alterations within hematopoietic stem cells (HSCs). Many somatic mutations in AML patients result in blocked myeloid differentiation or confer self-renewal upon primitive hematopoietic stem and progenitor cells (HSPCs). In case of CML patients, genetic alterations of the same type of cells, i.e. HSPCs, lead to increased proliferation thereof. Similar mechanisms are suggested in the development of other myeloid diseases. The acquisition of additional genetic aberrations within the pool of pre-leukemic HSPCs eventually gives rise to leukemic stem cells (LSCs) which have a role in a wide range of myeloid diseases including AML, CML, myeloproliferative neoplasm (MPN), myelodysplastic syndrome (MDS), chronic myelomonocytic leukemia (CMML), and others.

Despite rapid advances in the field including new drug targets and an increased understanding of AML as well as CML biology, the general approach to current treatment strategy has not changed substantially for myeloid diseases. The standard therapy of AML, for example, consists of an induction phase, involving a combination of cytarabine and anthracycline, in a standard intensive regimen termed '7+3' chemotherapy, followed by consolidation chemotherapy.

This conventional approach achieves complete remission (CR) in 60%-80% of younger adults and 40%-60% of elderly patients (commonly defined as >60 years of age; Dohner, H. et al. (2017). *Blood* 129, 424-447). However, the majority are not cured and long-term overall survival (OS) has changed minimally over the last several decades, with 5- and 3-year OS rates of 23-35%. In elderly patients, who comprise the majority of those diagnosed with AML, outcomes are improving, but remain particularly grim, with current expectations persisting at a median OS of <1 year from diagnosis.

As a strategy to extend the time of remissions, allogenic stem cell transplantations are usually considered. However, such transplantations are subject to other restrictions and complications such as accessibility of suitable donor cells, comorbidities and mixed responses to stem cell therapy.

One major obstacle to durable remissions in patients suffering from myeloid diseases or neoplasms, in particular from AML and CML, is the persistence of LSCs even after rigorous treatment. Standard chemotherapy can efficiently eliminate the bulk of neoplastic cells (proliferating leukemic blasts), however, LSCs are relatively resistant to these therapies and can reinitiate and maintain disease (Shlush, L. I. et al. (2014). *Nature* 506, 328-333). Still, polychemotherapy is the standard general treatment of patients suffering from myeloic diseases with all of the disadvantages thereof such as high toxicity and low success rates. Thus, it is imperative to find alternative approaches for inducing durable remissions and preventing relapse which target AML and LSCs which may be causative for relapses in various myeloid stem cell diseases.

Various myeloid stem cell diseases originate from the hematopoietic stem cell pool including HSPCs. While the individual genetic aberrations differ between the various types of diseases at later stages, the aberrant growth behavior is largely identical among these myeloid stem cell diseases. Thus, an approach directed at earlier stages of said diseases and relating to the hematopoietic stem cell pool appears promising in this context.

Presently, only very few targeted therapies are available, each of which are only useful for small subgroups of patients which exhibit specific biomarkers. Also, such targeted therapies may cause significant side effects which impair life quality of treated patients and may make such therapies overall unsuitable for the application in elderly patients.

Thus far, studies into cell death in AML have been focused on apoptosis, however, significant interest has emerged in recent years in the activation of alternative forms of cell death, such as necroptosis, as novel therapeutic strategy (Höckendorf, U. et al. (2016). *Cancer Cell* 30, 75-91.).

Necroptosis is a form of programmed necrosis mediated by the interaction of RIPK1 (receptor-interacting protein kinase 1) and RIPK3 under conditions in which caspase-8 is not active. Necroptosis is triggered by death receptor activation, the same stimuli that normally activate apoptosis, however, necroptosis is clearly distinct from apoptosis, as it does not involve key apoptosis regulators such as caspases and Bcl-2 family members, or cytochrome c release from mitochondria. Moreover, necroptosis is morphologically distinct from apoptosis, involving membrane rupture and release of cytoplasmic contents, including cytokines, chemokines and danger signals from dying cells (damage-associated molecular patterns; DAMPs), that drive inflammation.

The inventors have previously shown that HSPC undergoing FLT3-ITD- or AML-ETO-driven transformation initiate RIPK3-mediated necroptosis and inflammasome activation as a tumor-suppressive mechanism. In this context, necroptosis exhibited a dual functionality by causing LSC death and, in addition, propagating myeloid differentiation by the release of substantial amounts of IL-1β, further limiting leukemogenesis. Consequently, AML arose from LSCs that successfully suppressed the necroptotic pathway.

Departing from and based on the previous research and the state of the art in the field of therapy of myeloid diseases and myeloid neoplasms, it is thus an object of the present invention to provide useful and advantageous agents for use in therapy of such myeloid diseases and neoplasms which allow for more durable and deeper remissions of the disease, are associated with little or no side effects and are promising to lead to an increased long-term overall survival of these patients.

SUMMARY OF THE INVENTION

These objects have been solved by the aspects of the present invention as specified hereinafter.

According to the first aspect of the present invention, a polypeptide is provided comprising the amino acid sequence of SEQ ID No. 1 (full length human LT-α) or of SEQ ID No. 2 (mature form of human LT-α) or comprising an amino acid sequence having at least 80% identity to the amino acid sequence of SEQ ID No. 1 or SEQ ID No. 2 for use in the treatment of myeloid diseases or myeloid neoplasms.

According to a preferred embodiment of the first aspect of the present invention, the myeloid disease is a myeloid stem cell disease, preferably one of myeloproliferative neoplasm (MPN), myelodysplastic syndrome (MDS), blastic plasmacytoid dendritic cell neoplasm (BPDCN), acute myeloid leukemia (AML), chronic myeloid leukemia (CML), chronic myelomonocytic leukemia (CMML), myeloid neoplasms associated with eosinophilia and rearrangement of PDGFRA, PDGFRB, or FGFR1, or with PCM1-JAK2, more preferably the myeloid disease is one of acute myeloid leukemia (AML) or chronic myeloid leukemia (CML), even more preferably the myeloid disease is acute myeloid leukemia (AML).

According to another preferred embodiment of the first aspect of the present invention, the polypeptide is able to affect a TNF receptor superfamily (TNFRSF) dependent signal cascade, preferably a TNF receptor (TNFR) 1 (TNFRSF1A), TNFR2 (TNFRSF1B), lymphotoxin beta receptor (TNFRSF3) or HVEM (TNFRSF14)-dependent signal cascade, more preferably the signal cascade is TNFR1 and/or TNFR2-dependent.

According to a preferred embodiment of the first aspect of the present invention, the relevant signaling pathway affected by the polypeptide is fully or partially functional in an individual to be treated.

According to one preferred embodiment of the first aspect of the present invention, the polypeptide is able to induce programmed cell death, preferably the polypeptide is able to induce programmed cell death exclusively in one or more of leukemia cells, leukemic progenitor cells, and leukemic stem cells.

According to a preferred embodiment of the first aspect of the present invention, the polypeptide is a recombinant polypeptide or a purified endogenous polypeptide, preferably a recombinant polypeptide.

According to another preferred embodiment of the first aspect of the present invention, the polypeptide is for use in the treatment of a mammal, more preferably the polypeptide is for use in the treatment of a human.

According to yet another preferred embodiment of the first aspect of the present invention, the polypeptide consists of the amino acid sequence of SEQ ID No. 1 or of SEQ ID No. 2 or of an amino acid sequence having at least 80% identity to the amino acid sequence of SEQ ID No. 1 or of SEQ ID No. 2, preferably the polypeptide consists of the amino acid sequence of SEQ ID No. 2.

According to the second aspect of the present invention, a pharmaceutical composition is provided for use in the treatment of myeloid diseases or myeloid neoplasms, wherein the pharmaceutical composition comprises a polypeptide according to the first aspect of the present invention and at least one pharmaceutically acceptable excipient.

According to a preferred embodiment of the second aspect of the present invention, the pharmaceutical composition further comprises one or more substances selected from the group comprising one or more SMAC mimetic/s such as Birinapant, one or more chemotherapy agent/s such as Cytarabine (cytosine arabinoside) or Cerubidine (daunorubicine), and one or more TNF inhibitor/s such as Humira (adalimumab), Remicade (infliximab), Simponi (golimumab), Cimzia (certolizumab pegol).

According to another preferred embodiment of the second aspect of the present invention, the pharmaceutical composition is administered to the patient by way of systemic administration, preferably the pharmaceutical composition is administered to the patient by way of intravenous administration or subcutaneous administration, more preferably by intravenous administration.

According to yet another preferred embodiment of the second aspect of the present invention, the pharmaceutical composition does not comprise any type of TNF receptor molecule including the TNFR1 (SEQ ID No. 3), TNFR2 (SEQ ID No. 4), lymphotoxin beta receptor (SEQ ID No. 5), HVEM (SEQ ID No. 6), or antibodies directed against lymphotoxin or against any type of TNF receptor including the TNFR1, TNFR2, HVEM, and lymphotoxin beta receptor.

According to the third aspect of the present invention, a kit comprising a polypeptide according to the first aspect of the present invention and a container is provided for use in the treatment of myeloid diseases or myeloid neoplasms.

DETAILED DESCRIPTION OF THE INVENTION

Figure 1:
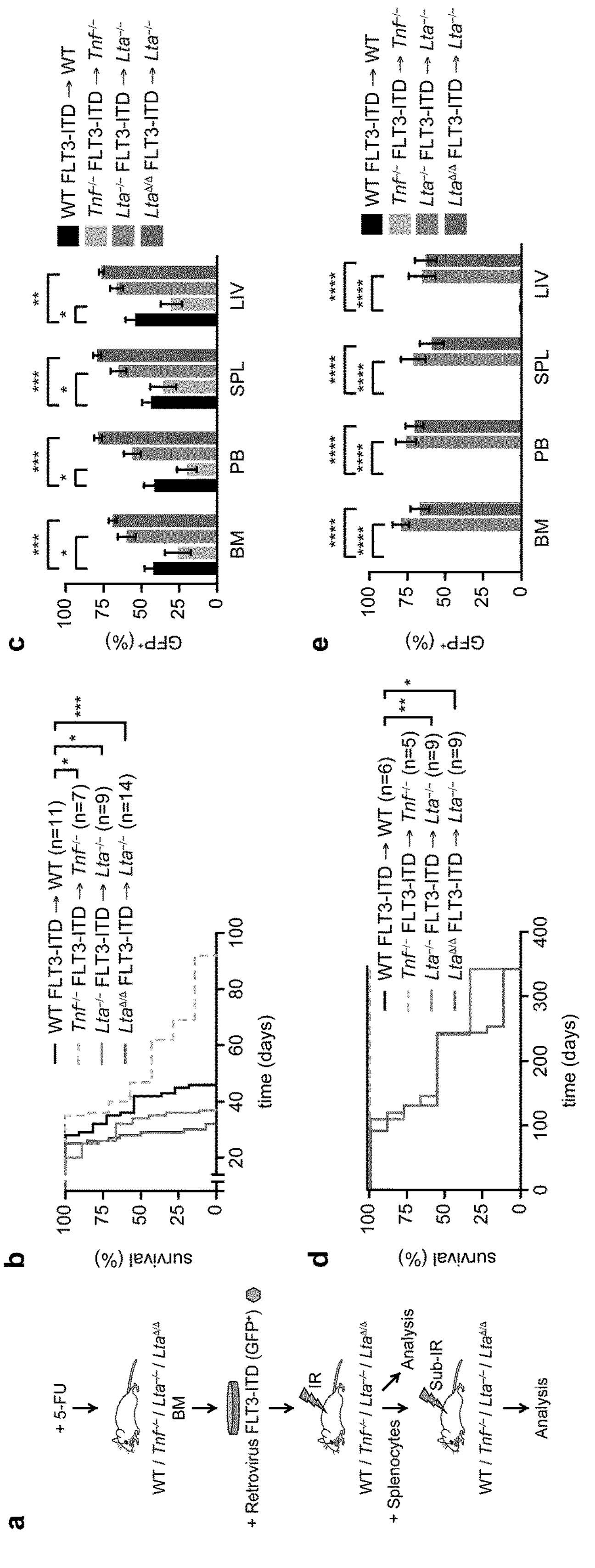
FIG. 1 shows that LT-α deficiency accelerates FLT3-ITD-induced myeloproliferation due to accumulation of leukemic stem and progenitor cells while TNF deficiency attenuates FLT3-ITD induced myeloproliferation due to failure of leukemic cell production in the bone marrow; (a) Experimental design; (b) Survival of mice transplanted with FLT3-ITD-transduced WT, $Tnf^{-/-}$ $LTa^{-/-}$ or $Lta^{\Delta/\Delta}$ BM. Median survival WT FLT3-ITD→WT 42 days versus $Tnf^{-/-}$ FLT3-ITD→$Tnf^{-/-}$ 47 days versus $LTa^{-/-}$ FLT3-ITD→$LTa^{-/-}$ 34 days versus $LTa^{\Delta/\Delta}$ FLT3-ITD→$LTa^{-/-}$ 28.5 days. Data are representative of two independent experiments. Number of mice as indicated in the figure; (c) frequency of $GFP^+$ cells in the bone marrow (BM), peripheral blood (PB), spleen (SPL), and liver (LIV); (d) Survival of mice serially transplanted with $GFP^+$ splenocytes from primary FLT3-ITD-transplanted mice in (b). $LTa^{-/-}$ FLT3-ITD→$LTa^{-/-}$ median survival 257 days, $LTa^{\Delta/\Delta}$ FLT3-ITD→$LTa^{-/-}$ median survival 260 days. Data are representative of two independent experiments. Number of mice as indicated in the figure; (e) Frequency of $GFP^+$ cells in the BM, PB, SPL, and LIV from mice in (d); each dot represents a mouse, and error bars represent mean±SEM. p values Mantel-Cox test (b, d), otherwise Student's t test. *$p<0.05$, $p<0.01$, *$p<0.001$, ****$p<0.0001$.

The present inventors have dedicated themselves to solving the problem of the present invention and were successful to find that the polypeptide as defined herein for use in the treatment of myeloid diseases or myeloid neoplasms leads to programmed cell death and reliable destruction of leukemic cells and leukemic stem cells (LSCs) which is promising to effect deep and durable remissions in patients suffering from these conditions.

The main advantages of the present invention are the highly specific effect on leukemia cells with a lack or negligible toxicity to healthy cells as well as an applicability to most patients suffering from myeloid diseases or neoplasms originating from hematopoietic stem and progenitor cells (HSPCs) such as AML or CML, and significant remission up to a cure of patients due to the pronounced effects on LSCs.

As already stated above, RIPK3-mediated necroptosis and inflammasome activation act as a tumor-suppressive mechanism. Importantly, consistent with their roles in RIPK3 activation, LSC survival and differentiation are controlled by TNF receptor (TNFR) 1 and 2 signaling. TNFR1 is ubiquitously expressed, conversely, expression of TNFR2 is highly regulated, induced upon inflammatory stimulation and is limited to hematopoietic lineage cells (typically lymphocytes) and endothelial cells. TNFR1 and TNFR2 transduce signals from two cognate ligands: the TNF trimer, and the lymphotoxin-α (LTα) trimer.

TNF is a pleiotropic cytokine that is produced by a wide range of cell types and exerts beneficial activities in immune regulation and host defense, as well as hazardous pro-inflammatory and cytotoxic functions during inflammation. It exists in both transmembrane and soluble forms. Both forms of TNF are biologically active, however, the soluble form of TNF has a higher affinity for TNFR1, whereas TNFR2 can only be properly activated by membrane-bound TNF.

In comparison to TNF, LT-α appears to have a far more restricted role. LT-α is produced primarily by CD4 T cells, B cells, natural killer (NK) cells and has specific roles in the development and function of the immune system, mainly in lymphoid organ development, organization and maintenance of lymphoid microenvironments, host defense, and inflammation. Besides binding to TNFR1 and TNFR2, LT-α binds to HVEM (herpesvirus entry mediator), but this binding is relatively weak. In contrast to TNF, LT-α is converted into its soluble form with high efficiency. LT-α is anchored to the cell membrane only as heterotrimer in association with membrane-bound LT-β, the predominant LTα1β2 form and a minor LTα2β1 form, both of which interact with the LT-β receptor (LTβR), but not TNFR1 or TNFR2.

Like TNF, LT-α binds with high affinity to TNFR1 and TNFR2. However, depending upon the specific cellular context, the outcome of TNFR activation can be survival, death, or differentiation. The pleiotropic nature of TNFR signaling results from the sequential formation of different signaling complexes/cascades upon activation of TNFR1 and 2. TNFR1 contains a death domain (DD), whereas TNFR2 does not.

The activation of TNFR1 can result in inflammation via induction of NF-κB and mitogen-activated protein kinases (MAPKs) JNK and p38 signaling, and cell death, which can either be apoptotic or necroptotic. While TNFR2 can also activate canonical NF-κB and JNK signaling, activation of TNFR2 is primarily considered to trigger non-canonical NF-κB signaling via E3 ligases TRAF2 and TRAF3, leading to numerous changes in gene expression that drive cell survival, proliferation, inflammation, immune regulation and tissue homeostasis. In addition, TNFR2 can elicit intracellular crosstalk between both receptors by directly binding with TRAF2 along with TRAF1, influencing the signaling outcome initiated by TNF binding.

Both TNFR1 and TNFR2 restrict the self-renewal capacity of healthy HSPCs in vivo. Interestingly, current data suggest that TNFR1 and TNFR2 differentially block HSPCs; TNF controls committed progenitor cells mostly by engaging TNFR1, whereas primitive hematopoietic progenitor cells obtain TNF signals via TNFR2. Moreover, the TNF/TNFR2 axis is involved in the correct development of embryonic HSCs.

TNFR1/2 signaling is skewed in myeloid diseases or myeloid neoplasms such as several AML subtypes by up-regulating TNFR2 surface expression and turning TNF-dependent signaling towards promoting HSPC self-renewal rather than suppressing it. In this oncogenic context, LT-α was surprisingly found to be a ligand capable of engaging TNFR1/2 in order to induce cell death.

The present inventors successfully developed clinically relevant models of AML and CML as exemplary myeloid stem cell diseases to demonstrate based on in vitro and in vivo data that targeting LSCs with LT-α is effective in the treatment of myeloid stem cell diseases such as AML or CML and how it can be most effectively used to increase the chances of cure in diseases such as AML, CML and others. Using these models as well as primary AML patient samples, they are able to show that LT-α can in fact kill AML LSCs as well as blast cells of CML and induce deep and durable remissions in myeloid neoplasms and myeloid diseases.

Thus, the present invention is directed to a polypeptide comprising the amino acid sequence of SEQ ID No. 1 (full length human LT-α) or of SEQ ID No. 2 (mature form of human LT-α) or comprising an amino acid sequence having at least 80% identity to the amino acid sequence of SEQ ID No. 1 or SEQ ID No. 2 for use in the treatment of myeloid diseases or myeloid neoplasms.

In the context of the present invention, SEQ ID No. 1 represents full length human LT-α including the signal peptide of amino acids 1 to 34. According to a preferred embodiment, the polypeptide for use according to the invention comprises SEQ ID No. 1, preferably the polypeptide for use according to the invention consists of SEQ ID No. 1.

The amino acid sequence of SEQ ID No. 1 is the following:

```
MTPPERLFLPRVCGTTLHLLLLGLLLVLLPGAQGLPGVGLTPSAAQTARQ

HPKMHLAHSTLKPAAHLIGDPSKQNSLLWRANTDRAFLQDGFSLSNNSLL

VPTSGIYFVYSQVVFSGKAYSPKATSSPLYLAHEVQLFSSQYPFHVPLLS

SQKMVYPGLQEPWLHSMYHGAAFQLTQGDQLSTHTDGIPHLVLSPSTVFF

GAFAL
```

In the context of the present invention, SEQ ID No. 2 represents the mature form of human LT-α wherein the signal peptide has been replaced by an N-terminal Methionin. According to a preferred embodiment, the polypeptide for use according to the invention comprises SEQ ID No. 2, preferably the polypeptide for use according to the invention consists of SEQ ID No. 2.

The amino acid sequence of SEQ ID No. 2 is the following:

```
MLPGVGLTPSAAQTARQHPKMHLAHSTLKPAAHLIGDPSKQNSLLWRANT

DRAFLQDGFSLSNNSLLVPTSGIYFVYSQVVFSGKAYSPKATSSPLYLAH

EVQLFSSQYPFHVPLLSSQKMVYPGLQEPWLHSMYHGAAFQLTQGDQLST

HTDGIPHLVLSPSTVFFGAFAL
```

The full length amino acid sequence of LT-α in humans (SEQ ID NO. 1) can be obtained under the UniProt accession number P01374. The mature sequence of SEQ ID No. 2 may be obtained as amino acids 35-205 of the entry under the UniProt accession number P01374 with the addition of an N-terminal Methionine.

In the present invention, polypeptides comprising amino acid sequences having at least 80% identity to SEQ ID No. 1 or SEQ ID No. 2 are also envisaged as polypeptides for use according to the invention. According to one preferred embodiment, the polypeptide for use according to the invention comprises an amino acid sequence having at least 80% identity to SEQ ID No. 1, preferably at least 85%, more preferably at least 90%, even more preferably at least 95% and even more preferably at least 99% identity to SEQ ID No. 1. Even more preferably, the polypeptide for use according to the invention consists of an amino acid sequence having a degree of identity as described above.

According to another preferred embodiment, the polypeptide for use according to the invention comprises an amino acid sequence having at least 80% identity to SEQ ID No. 2, preferably at least 85%, more preferably at least 90%, even more preferably at least 95% and even more preferably at least 99% identity to SEQ ID No. 2. Even more preferably, the polypeptide for use according to the invention consists of an amino acid sequence having a degree of identity as described above.

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

Due to the mechanism of action of LT-α on aberrant myeloid cells such as leukemic cells and LSCs, it is plausible to apply this molecule also to patients suffering from different myeloid diseases, in particular those derived from aberrant myeloid stem or progenitor cells. Thus, according to a preferred embodiment the myeloid disease is a myeloid stem cell disease, preferably one of myeloproliferative neoplasm (MPN), myelodysplastic syndrome (MDS), blastic plasmacytoid dendritic cell neoplasm (BPDCN), acute myeloid leukemia (AML), chronic myeloid leukemia (CML), chronic myelomonocytic leukemia (CMML), myeloid neoplasms associated with eosinophilia and rearrangement of PDGFRA, PDGFRB, or FGFR1, or with PCM1-JAK2, more preferably the myeloid disease is one of acute myeloid leukemia (AML) or chronic myeloid leukemia (CML), even more preferably the myeloid disease is acute myeloid leukemia (AML). Within the present invention, a myeloid stem cell disease is a myeloid disease which originates from hematopoietic stem and progenitor cells (HSPCs) in the bone marrow.

According to a specifically preferred embodiment, the polypeptide for use according to the present invention is able to affect a TNF receptor superfamily dependent signal cascade, more preferably a TNFR1 (TNFRSF1A), TNFR2 (TNFRSF1B), lymphotoxin beta-receptor (TNFRSF3) or HVEM (TNFRSF14) dependent signal cascade. Thus, it is preferable that the polypeptide for use according to the present invention is able to bind specifically and with high affinity to the TNFR1, TNFR2, lymphotoxin beta-receptor or HVEM, more preferably TNFR1 and/or TNFR2.

Since the polypeptide of the present invention carries out its function based on the TNF receptor superfamily member dependent signal cascade, it is preferable that said pathways are fully or at least partly functional in the subject to be treated. Preferably, it may be examined before administration of the polypeptide of the present invention, if the relevant pathways are fully or at least partly functional in the subject to be treated.

Preferably, the polypeptide for use according to the invention is able to induce programmed cell death in isolated aberrant cells or aberrant cells in vivo, preferably the polypeptide is able to induce programmed cell death exclusively in one or more of cells determined as leukemia cells, leukemic progenitor cells, and leukemic stem cells, more preferably of leukemic stem cells. It is also preferable that the polypeptide for use according to the present invention is able to act as a ligand capable of engaging the TNF receptor superfamily members TNFR1, TNFR2, lymphotoxin beta-receptor or HVEM, more preferably TNFR1 and/or TNFR2. Such engagement preferably induces cell death of specific aberrant cells.

The polypeptide for use according to the present invention may preferably be prepared and obtained by recombinant protein production as is commonly known in the art. Alternatively preferably, the polypeptide for use according to the present invention may be purified from endogenous sources.

In the context of the present invention, the polypeptide for use of the present invention is preferably for use in the treatment of a mammal, such as cats or dogs. According to one particular preferred embodiment, the polypeptide is for use in the treatment of human patients.

The present invention is also directed to a method of treatment of myeloid diseases or myeloid neoplasms, wherein an individual in need of such treatment is administered an effective amount of the polypeptide according to the invention or a pharmaceutical composition according to the invention.

The present invention is also directed to the use of a polypeptide according to the invention or a pharmaceutical composition according to the invention in the manufacture of a medicament for treatment of myeloid diseases or myeloid neoplasms.

Furthermore, the present invention is also directed to a pharmaceutical composition for use in the treatment of myeloid diseases or myeloid neoplasms, wherein the pharmaceutical composition comprises a polypeptide according to the present invention and at least one pharmaceutically acceptable excipient such as a suitable carrier or diluent.

Preferably the polypeptide for use according to the invention constitutes an active ingredient of the pharmaceutical composition and/or is present in an effective amount. The term "effective amount" denotes an amount of the polypeptide for use according to the invention having a prophylactically, diagnostically or therapeutically relevant effect on a disease or pathological conditions.

A prophylactic effect prevents the outbreak of a disease. A therapeutically relevant effect relieves to some extent one or more symptoms of a disease or returns to normal either partially or completely one or more physiological or biochemical parameters associated with or causative of the disease or pathological conditions. The respective amount for administering the polypeptide for use according to the invention is sufficiently high in order to achieve the desired prophylactic, diagnostic or therapeutic effect. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. Using well-known means and methods, the exact amount can be determined by one of skill in the art as a matter of routine experimentation.

In the pharmaceutical composition for use according to the invention, the content of the polypeptide for use according to the present invention is preferably such that it is suitable for administration to a patient at a dosage of from 250 ng/kg body weight to 250 μg/kg body weight, more preferably from 100 ng/kg body weight to 100 μg/kg body weight, even more preferably from 500 ng/kg body weight to 50 μg/kg body weight, even more preferably from 1 μg/kg body weight to 10 μg/kg body weight, even more preferably from 3 μg/kg body weight to 8 μg/kg body weight, in particular at about 5 μg/kg body weight. Thus, the polypeptide of the present invention is preferably administered to a patient at a dosage of from 250 ng/kg body weight to 250 μg/kg body weight, more preferably from 100 ng/kg body weight to 100 μg/kg body weight, even more preferably from 500 ng/kg body weight to 50 μg/kg body weight, even more preferably from 1 μg/kg body weight to 10 μg/kg body weight, even more preferably from 3 μg/kg body weight to 8 μg/kg body weight, in particular at about 5 μg/kg body weight.

The pharmaceutical composition of the present invention will generally be administered as a formulation in association with one or more pharmaceutically acceptable excipients. The term "excipient" is used herein to describe any ingredient other than the polypeptide for use according to the invention. The choice of excipient will to a large extent depend on the particular mode of administration. Excipients can be suitable carriers and/or diluents.

The pharmaceutical composition for use according to the invention may preferably be administered to the patient to provide systemic effectiveness. To this end, the pharmaceutical composition is preferably administered by way of systemic administration, more preferably by intravenous, intraarterial, intraperitoneal, intrathecal, intraventricular, intraurethral, intrasternal, intracranial, intramuscular or subcutaneous administration, even more preferably by subcutaneous administration or intravenous administration, in particular by intravenous administration.

Suitable devices for administration include needle (including microneedle) injectors, needle-free injectors and infusion techniques. Parenteral formulations useful herein are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art. The solubility of pharmaceutical composition for use according to the invention used in the preparation of parenteral solutions may be increased by the use of appropriate formulation techniques, such as the incorporation of solubility-enhancing agents.

According to a preferred embodiment of the present invention, the pharmaceutical composition further comprises one or more substances selected from the group comprising one or more SMAC mimetic/s such as Birinapant, one or more chemotherapy agent/s such as Cytarabine (cytosine arabinoside) or Cerubidine (daunorubicine), and one or more TNF inhibitor/s such as Humira (adalimumab), Remicade (infliximab), Simponi (golimumab), Cimzia (certolizumab pegol).

Preferably, the pharmaceutical composition does not comprise any type of TNF receptor superfamily molecule. More preferably, the pharmaceutical composition does not comprise SEQ ID No. 3. SEQ ID No. 3 represents the amino acid sequence of TNFR1 which has the UniProt accession number P19438.

The amino acid sequence of SEQ ID No. 3 is the following:

```
MGLSTVPDLLLPLVLLELLVGIYPSGVIGLVPHLGDREKRDSVCPQGKYI
HPQNNSICCTKCHKGTYLYNDCPGPGQDTDCRECESGSFTASENHLRHCL
SCSKCRKEMGQVEISSCTVDRDTVCGCRKNQYRHYWSENLFQCFNCSLCL
NGTVHLSCQEKQNTVCTCHAGFFLRENECVSCSNCKKSLECTKLCLPQIE
NVKGTEDSGTTVLLPLVIFFGLCLLSLLFIGLMYRYQRWKSKLYSIVCGK
STPEKEGELEGTTTKPLAPNPSFSPTPGFTPTLGFSPVPSSTFTSSSTYT
PGDCPNFAAPRREVAPPYQGADPILATALASDPIPNPLQKWEDSAHKPQS
LDTDDPATLYAVVENVPPLRWKEFVRRLGLSDHEIDRLELQNGRCLREAQ
YSMLATWRRRTPRREATLELLGRVLRDMDLLGCLEDIEEALCGPAALPPA
PSLLR
```

Also preferably, the pharmaceutical composition does not comprise SEQ ID No. 4. SEQ ID No. 4 represents the amino acid sequence of TNFR2 which has the UniProt accession number P20333.

The amino acid sequence of SEQ ID No. 4 is the following:

```
MAPVAVWAALAVGLELWAAAHALPAQVAFTPYAPEPGSTCRLREYYDQTA
QMCCSKCSPGQHAKVFCTKTSDTVCDSCEDSTYTQLWNWVPECLSCGSRC
SSDQVETQACTREQNRICTCRPGWYCALSKQEGCRLCAPLRKCRPGFGVA
RPGTETSDVVCKPCAPGTFSNTTSSTDICRPHQICNVVAIPGNASMDAVC
TSTSPTRSMAPGAVHLPQPVSTRSQHTQPTPEPSTAPSTSFLLPMGPSPP
AEGSTGDFALPVGLIVGVTALGLLIIGVVNCVIMTQVKKKPLCLQREAKV
PHLPADKARGTQGPEQQHLLITAPSSSSSSLESSASALDRRAPTRNQPQA
PGVEASGAGEARASTGSSDSSPGGHGTQVNVTCIVNVCSSSDHSSQCSSQ
ASSTMGDTDSSPSESPKDEQVPFSKEECAFRSQLETPETLLGSTEEKPLP
LGVPDAGMKPS
```

Also preferably, the pharmaceutical composition does not comprise SEQ ID No. 5. SEQ ID No. 5 represents the amino acid sequence of lymphotoxin beta receptor which has the UniProt accession number P36941.

The amino acid sequence of SEQ ID No. 5 is the following:

```
MLLPWATSAPGLAWGPLVLGLFGLLAASQPQAVPPYASENQTCRDQEKEY
YEPQHRICCSRCPPGTYVSAKCSRIRDTVCATCAENSYNEHWNYLTICQL
CRPCDPVMGLEEIAPCTSKRKTQCRCQPGMFCAAWALECTHCELLSDCPP
```

-continued

```
GTEAELKDEVGKGNNHCVPCKAGHFQNTSSPSARCQPHTRCENQGLVEAA
PGTAQSDTTCKNPLEPLPPEMSGTMLMLAVLLPLAFFLLLATVFSCIWKS
HPSLCRKLGSLLKRRPQGEGPNPVAGSWEPPKAHPYFPDLVQPLLPISGD
VSPVSTGLPAAPVLEAGVPQQQSPLDLTREPQLEPGEQSQVAHGTNGIHV
TGGSMTITGNIYIYNGPVLGGPPGPGDLPATPEPPYPIPEEGDPGPPGLS
TPHQEDGKAWHLAETEHCGATPSNRGPRNQFITHD
```

Also preferably, the pharmaceutical composition does not comprise SEQ ID No. 6. SEQ ID No. 6 represents the amino acid sequence of HVEM (herpes virus entry mediator, also known in the art as TNFRSF14 (tumor necrosis factor receptor superfamily member 14) or CD270) which has the UniProt accession number Q92956.

The amino acid sequence of SEQ ID No. 6 is the following:

```
MEPPGDWGPPPWRSTPKTDVLRLVLYLTFLGAPCYAPALPSCKEDEYPVG
SECCPKCSPGYRVKEACGELTGTVCEPCPPGTYIAHLNGLSKCLQCQMCD
PAMGLRASRNCSRTENAVCGCSPGHFCIVQDGDHCAACRAYATSSPGQRV
QKGGTESQDTLCQNCPPGTFSPNGTLEECQHQTKCSWLVTKAGAGTSSSH
WVWWFLSGSLVIVIVCSTVGLIICVKRRKPRGDVVKVIVSVQRKRQEAEG
EATVIEALQAPPDVTTVAVEETIPSFTGRSPNH
```

According to one preferred embodiment, the pharmaceutical composition does not comprise a protein comprising any of the sequences of SEQ ID No. 3, SEQ ID No. 4, SEQ ID No. 5 or SEQ ID No. 6 or any of the respective mature protein sequences lacking the signal peptide sequences.

Also preferably, the pharmaceutical composition for use according to the present invention does not comprise antibodies directed against lymphotoxin or against any type of TNF receptor including the TNFR1, TNFR2, lymphotoxin beta receptor and HVEM. Most preferably, the pharmaceutical composition for use according to the present invention does not comprise any of SEQ ID No. 3, 4, 5, or 6 or antibodies directed against lymphotoxin or against any type of TNF receptor including TNFR1, TNFR2, the lymphotoxin beta receptor and HVEM.

The present invention is also directed to a kit for use according to the invention comprising a polypeptide for use according to the invention, a container and optionally written instructions for use and/or with means for administration.

All embodiments of the present invention as described herein are deemed to be combinable in any combination, unless the skilled person considers such a combination to not make any technical sense.

EXAMPLES

I. Materials & Methods

I.1. Cell Culture

All cells were cultured at 37° C. and 5% CO2 in a fully humidified atmosphere.

Human primary samples: Bone marrow mononuclear cells (BMMC) were isolated from heparinized bone marrow samples or bone chips by centrifugation over a Ficoll-Hypaque layer (Biochrom) of 1.077 g/ml density. Cells were harvested and used directly for immunephenotyping or cultured in IMDM (Gibco) supplemented with 20% fetal calf serum (FCS; PAN-Biotech), penicillin/streptomycin 0.05 mM, L-glutamine 2 mM, and 2-mercaptoethanol 0.05 mM (Gibco) on EL08-1D2 stromal cells.

The murine embryonic liver stromal cell line EL08-1D2 was obtained from Prof. R. Oostendorp (TUM, Germany) and cultured in MEM Alpha+GlutaMAX medium (Gibco) supplemented with 10% fetal calf serum, 10% horse serum (StemCell technologies), 2-mercaptoethanol 0.05 mM, and penicillin/streptomycin 0.05 mM. These cells were grown on gelatine coated (0.1% in PBS; Sigma) cell culture plates. Prior to co-culture with primary human BMMC, EL08-1D2 cells were irradiated (30 Gy) and incubated for at least 3 hr before use.

AML and CML cell lines were maintained as indicated by ATCC or DSMZ bioresource centers. All cell lines were regularly tested for mycoplasma using the MycoProbe Mycoplasma Detection Kit (R&D Systems) and authenticated utilizing Short Tandem Repeat (STR) profiling (ATCC). PLB-985, although present in the database of commonly misidentified cell lines maintained by ICLAC, was included in this study as a necessary model of an oncogenic driver-independent AML. DNA fingerprinting of this cell line showed unequivocally that PLB-985 is a subclone of cell line HL-60, but shows different characteristics, including cytogenetics (e.g. Myc negative), DNA profile, differentiation, and treatment response. This cell line was authenticated by DNA fingerprinting and compared to published STR profile (Cellosaurus).

Progenitor Cell Analysis (HUMAN)

For measuring cytokines, BM supernatant fluid was obtained from the BM aspirated samples by centrifugation. Supernatants were concentrated with Vivaspin 10 kDa filters (Sartorius) and cytokines were quantified using Cytometric Bead Array (CBA; BD Biosciences) according to the manufacturer's instructions.

For immunophenotyping, BM cells or AML cell lines were rinsed three times with PBS, viability-stained using Zombie NIR™ Fixable Viability Kit (Biolegend) according to the manufacturer's instructions, preincubated with Fc-block, and subsequently stained with fluorescently labelled antibodies as listed below. All centrifugation steps were performed at 400×g.

For flow cytometry analysis after treatment, BM cells or AML cell lines were cultured as described above for 7 days in the presence of the following cytokines and inhibitors if indicated and not stated otherwise: Etanercept (Enbrel®; 50 ng/ml; Pfizer), recombinant human (rh) LT-α (100 ng/ml; R&D), rh TNF (100 ng/ml; R&D), Emricasan (2.5 nM; SelleckChem), Birinapant (10 nM; SelleckChem), Cytarabine (100 nM), a-LTα-Ig (10 μg/ml; 359-238-8; Biolegend), Adalimumab (Humira®; 500 ng/ml; Abbvie), and respective isotype controls Mouse IgG1, κ (MOPC-21; Biolegend), and Ultra-LEAF™ purified Human IgG1 (QA16A12; Biolegend).

Progenitor Cell Analysis (MOUSE)

For colony forming cell assays, all duplicate cultures were performed in 35 mm petri dishes in murine methylcellulose medium (Methocult, Stem Cell Technologies). BM cells of unchallenged or 5-FU-challenged mice were plated in M3434. FLT3-ITD-infected BM cells were plated in M3234 medium in the presence of the following cytokines and inhibitors if indicated and not stated otherwise: recombinant mouse (rm) LT-α (100 ng/ml), rm TNF (100 ng/ml; R&D), Etanercept (50 ng/ml), Colonies were counted after 10 days by light microscopy. Empty vector-infected cells were used as negative controls and did not yield any colony formation. For analysis of colony forming units (CFU) cell viability, colonies were grown for 10 days in the presence of propidium iodide (PI) (0.8 μg/ml; Sigma) and representative CFU-GEMM were imaged using a Keyence BZ-9000 (Biorevo) fluorescence microscope.

I.2. Other

Mice

Tnf tm1Gkl Tnf$^{-/-)}$, $^{Tnfrsf}$1 atm1Mak/J (Tnfr1$^{-/-}$), Tnfrsf1 btm1Mwm/J (Tnfr2$^{-/-}$), and Lta$^{tm1Dch}$/J (Lta$^{-/-}$) mice were purchased from Jackson Laboratories. Tnfr1/2$^{-/-}$ mice were kindly provided by Prof. M. Heikenwälder (DKFZ Heidelberg, Germany), Lta$^{\Delta/\Delta}$ mice were obtained from Dr. A. Kruglov (DRFZ Berlin, Germany). Ripk3$^{-/-}$ mice were obtained under a material transfer agreement from Genentech and have been previously described. All animal experiments were performed in compliance with protocols approved by the local animal ethics committee guidelines.

Human Primary Samples

Primary and secondary AML samples were obtained from patients enrolled in the clinical trial AMLCG-2008 (http://clinicaltrial.gov identifier NCT01382147), the AML register protocol of the AML Register and Biomaterial Database of the German Leukemia Study Alliance, the AML register protocol of the German AML Cooperative Group Version 2.0 from Jan. 6, 2011, the AML register protocol of the German AML study group, or treated at the III. Medical Department at the Technical University of Munich after approval of the local ethics committee (approval no. 62/16 S from Feb. 10, 2016 to 2790/10 from Apr. 30, 2010). Informed consent was obtained from patients at study entry.

Non-leukemia control samples were collected from individuals who underwent bone marrow aspiration for diagnostic purposes and in whom subsequently a hematological disease was ruled out. Healthy controls were isolated from the femoral heads of patients who underwent surgical hip replacement.

In Vivo Treatment in FLT3-ITD Mouse Model

Retrovirus preparation, transduction and transplantation of murine bone marrow were performed as described previously (Höckendorf et al., 2016; supra).

For the in vivo treatment experiment, FLT3-ITD transduced C57BL/6 WT cells were resuspended in PBS (Sigma) and injected i.v. into C57BL/6 WT recipient mice that were busulfan conditioned prior to transplantation by i.p. administration of 20 mg/kg busulfan (Sigma) on five consecutive days as previously described (Peake, K., et al., (2015). J Vis Exp, e52553.).

For treatment, two- and eight-weeks post transplantation animals were randomly divided into groups of eight. Mice were i.v. injected twice per week with either isotype control (5 mg/kg; RTK2071; Biolegend), Etanercept (Enbrel®, 50 ng/ml; Pfizer), rm LT-α (250 μg/kg; Cusabio), a-TNF (5 mg/kg; MP6-XT22; Biolegend), or rm LT-α plus a-TNF.

Mice with disease were sacrificed. Peripheral blood white blood cell counts (WBC) were measured by scil Vet abc (scil animal care company). Single-cell suspensions of indicated tissue samples were prepared and red blood cells of peripheral blood were lysed before analysis. Cells were preincubated with Fc-block and subsequently stained with fluorescently labeled antibodies. Dead cells were excluded by PI (Sigma) or Zombie Aqua™ Fixable Viability Kit (Biolegend) staining according to the manufacturer's instructions. Flow cytometric immunophenotyping of transplanted mice was performed as described previously (Höckendorf et al., 2016; supra).

Statistical Analysis

For statistical analyses, p values were determined by applying the two-tailed t test for independent samples. Survival curves were analysed using the Mantel-Cox test, performed with GraphPad Prism software. Throughout the manuscript, all values are expressed as means±SEM, and statistical significance was defined as $p<0.0001$ (**), $p<0.001$ (*), $p<0.01$ (**), $p<0.05$ (*), or ns (statistically nonsignificant).

If not otherwise indicated all experiments represent at least eight mice per group.

I.3. Reagents and Antibodies

Antibodies used to separate mouse hematopoietic cell subsets: Fc-block and fluorescently labelled antibodies against B220 (RA3_6B2), CD19 (eBio1D3), Thy1.2 (53-2.1), CD3 (17A2), TCR-b (H57-597), CD4 (Gk1.5), CD8a (53-6.7), CD11b (M1/70), F4/80 (BM8), Gr-1 (RB6-8C5), Ly6B.2 (AbD Serotec), CD34 (700011; R&D Systems), Sca-1 (D7), c-Kit (2B8), CD16/32 (93), CD244.2 (eBio244F4), CD150 (mShad150), CD48 (HM48-1), Ly6C (HK1.4), Ter119 (TER-119), and IL-7Ra (A7R34) were purchased from eBioscience if not otherwise stated. The gating strategy used to identify murine hematopoietic stem and progenitor subsets has been previously described (Höckendorf et al., 2016; supra).

Antibodies used to separate human hematopoietic cell subsets, for immunephenotyping and intracellular protein expression analysis: Fluorescently labelled antibodies against Lineage Cocktail (Cat #348801; 348703), CD45RA (HI100), CD34 (581), CD38 (HB-7), CD99 (3B2/TA8), CD123 (5B11) were obtained from Biolegend. Flow analysis was performed on a BD FACS Canto II (BD Biosciences) and data were analyzed using FlowJo software (Tree Star).

II. Results

LT α Restricts Malignant Myeloproliferation

To determine the role of TNF and LT-α in AML, the inventors took advantage of the murine bone marrow transplantation model of the FLT3-ITD-driven myeloproliferative disorder in mice (Höckendorf et al., 2016; supra). As previously reported, transplantation of FLT3-ITD-transduced wild-type (WT) bone marrow into lethally irradiated syngeneic WT recipient mice (abbreviated as WT FLT3-ITD→WT) resulted in a rapid and fatal myeloproliferative neoplasm (MPN) characterized by peripheral leukocytosis, hepato-splenomegaly, and infiltration into the bone marrow (BM), spleen and liver (FIG. 1*a-c*).

To explore the role of LT-α in AML development, the inventors made use of two different strains of LT-α deficient mice. Unlike the conventional $Lta^{-/-}$ mice that are defective in TNF production, neo-free $Lta^{\Delta/\Delta}$ animals are capable of producing normal amounts of TNF both in vivo and in vitro.

LT-α deficient recipient mice transplanted with FLT3-ITD-transduced $Lta^{-/-}$ or $Lta^{\Delta/\Delta}$ BM (abbreviated as $Lta^{-/-}$ FLT3-ITD→$Lta^{-/-}$ and $Lta^{\Delta/\Delta}$ FLT3-ITD→$Lta^{-/-}$) succumbed significantly faster to a MPN compared to WT FLT3-ITD (FIG. 1*b*), which was associated with substantially aggravated clinical features, including elevated white blood cell (WBC) counts and an increased hepato-splenomegaly (data not shown). The elevated leukemic burden in $Lta^{-/-}$ FLT3-ITD→$Lta^{-/-}$ and $Lta^{\Delta/\Delta}$ FLT3-ITD→$Lta^{-/-}$ was also observed by flow cytometry for $GFP^{+}$ cells (FIG. 1*c*). Of note, $Lta^{\Delta/\Delta}$ FLT3-ITD→$Lta^{-/-}$ succumbed to a markedly aggravated disease compared to $Lta^{-/-}$ FLT3-ITD→$Lta^{-/-}$ (FIG. 1*b*).

In sharp contrast, TNF deficient recipient mice transplanted with FLT3-ITD-transduced $Tnf^{-/-}$ BM (abbreviated as $Tnf^{-/-}$ FLT3-ITD→$Tnf^{-/-}$) demonstrated a significantly delayed disease progression compared to WT FLT3-ITD. Histological examination of $Tnf^{-/-}$ FLT3-ITD→$Tnf^{-/-}$ showed a replacement of the BM hematopoietic tissue by connective tissue that bore resemblance to primary myelofibrosis (data not shown). The depressed leukemic burden in $Tnf^{-/-}$ FLT3-ITD→$Tnf^{-/-}$ was also observed by flow cytometry for $GFP^{+}$ cells (FIG. 1*c*).

Together, these data suggest that LT-α delayed AML progression, while TNF increased the clonogenic potential of LSCs, elevated the number of leukemic cells, and promoted AML development.

To determine the factors responsible for the differential disease characteristics of LT-α and TNF deficient animals, the inventors characterized the composition of the HSPC compartment in FLT3-ITD-transplanted mice. Similar to human AML, characterized by an accumulation of primitive HSPC, the inventors found a significant expansion of FLT3-ITD-expressing lineage-negative ($Lin^{-}$) cells in all tested organs in $Lta^{\Delta/\Delta}$ FLT3-ITD→$Lta^{-/-}$ and, to a lesser extent, also in $Lta^{-/-}$ FLT3-ITD→$Lta^{-/-}$ (data not shown).

Characterization of the $Lin^{-}Sca1^{+}$ $c\text{-}Kit^{+}$ (LSK) compartment (containing long- and short-term HSC (LT- and ST-HSC) and multipotent progenitor cells (MPP)) in comparison to the myeloid progenitor populations ($Lin^{-}Sca1^{-}c\text{-}Kit^{+}$) (containing common myeloid progenitors (CMP), granulocyte-macrophage progenitors (GMP), and megakaryocyteerythroid progenitors (MEP)) revealed that the expansion was mostly attributable to a marked increase in the CMP (BM: $Lta^{-/-}$ vs WT, $p=0.0115$; $Lta^{\Delta/\Delta}$ vs WT, $p<0.0001$) and ST-HSC population (BM: $Lta^{\Delta/\Delta}$ vs WT, $p=0.0287$) only in LTα deficient mice, while WT FLT3-ITD expanded the GMP compartment and depleted the HSC compartment (data not shown), as previously reported (Höckendorf et al., 2016; supra). Moreover, a distinct increase in the GMP population in $Tnf^{-/-}$ FLT3-ITD→$Tnf^{-/-}$ (BM: $Tnf^{-/-}$ vs WT, $p=0.0151$) was observed, despite significantly reduced absolute numbers of FLT3-ITD-expressing cells in all organs (data not shown). This was supported by the presence of leukemic blasts only in the BM of mice transplanted with $Lta^{-/-}$ FLT3-ITD and $Lta^{\Delta/\Delta}$ FLT3-ITD (data not shown).

Of note, upon serial transplantation of splenocytes from diseased mice, only $Lta^{-/-}$ FLT3-ITD and $Lta^{\Delta/\Delta}$ FLT3-ITD cells, but not WT controls or $Tnf^{-/-}$ FLT3-ITD, were able to reconstitute and give rise to a transplantable leukemia in secondary recipients (FIG. 1*d*). Indeed, leucocytosis and myeloid organ infiltration were detected only in $Lta^{-/-}$ FLT3-ITD→$Lta^{-/-}$ and $Lta^{\Delta/\Delta}$ FLT3-ITD→$Lta^{-/-}$ secondary transplants, as verified by organ infiltration of $GFP^{+}$ cells (FIG. 1*e*).

Since FLT3-ITD-driven MPN in WT mice is not serially transplantable (FIG. 1*d*), this finding illustrated the strongly enhanced capability of transformed HSPC to survive and to propagate a myeloid neoplasm when Lta was deleted.

FLT3-ITD Skews TNF-Dependent TNFR1/2 Signaling Towards Promoting HSPC Self-Renewal Although both TNFR1 and TNFR2 have been shown to play a role in restricting HSPC self-renewal, the role of LT-α in this process is not known. Therefore, the inventors explored the functional consequences of TNFR signaling on the survival and differentiation capacity of HSPC before and after FLT3-ITD expression, by assaying their colony-forming capacity.

At steady state BM from 5-FU-challenged (HSPC-enriched) WT, $Ripk3^{-/-}$, $Lta^{-/-}$, and $Lta^{\Delta/\Delta}$ mice showed normal differentiation and distribution into all myeloid lineages (data not shown). However, the number of multipotent granulocyte-erythrocyte-macrophage-megakaryocyte (GEMM) colonies was different across genotypes. HSPC-enriched BM $Lta^{-/-}$ and $Lta^{\Delta/\Delta}$ displayed GEMM colony numbers comparable to WT, while $Ripk3^{-/-}$ and $Tnf^{-/-}$ showed higher number of GEMM colonies (FIG. 2*a*).

When analzying the GEMM colonies after FLT3-ITD expression, an opposite effect for TNF and LT-α was observed. While $Ripk3^{-/-}$, $Lta^{-/-}$, and $Lta^{\Delta/\Delta}$ showed higher number of GEMM colonies, $Tnf^{-/-}$ showed numbers comparable to WT (FIG. 2*b-c*). In addition, fluorescence microscopy analysis of the same colonies showed higher cell death in WT and $Tnf^{-/-}$ compared to Lta deficient colonies (detected as propidium iodide incorporation, data not shown).

In contrast to non-transformed cells, in WT FLT3-ITD transduced cultures exogenous TNF specifically and significantly increased the number of GEMM colonies (FIG. 2*d*), but restricted the differentiated and mature progeny in a dose-dependent manner (data not shown). This is in agreement with previous studies in which TNF was observed to promote the survival and proliferation of patient derived AML blasts. Surprisingly, in WT FLT3-ITD transduced cultures exogenous LT-α significantly reduced the number of GEMM colonies (FIG. 2*d*).

Figure 2:
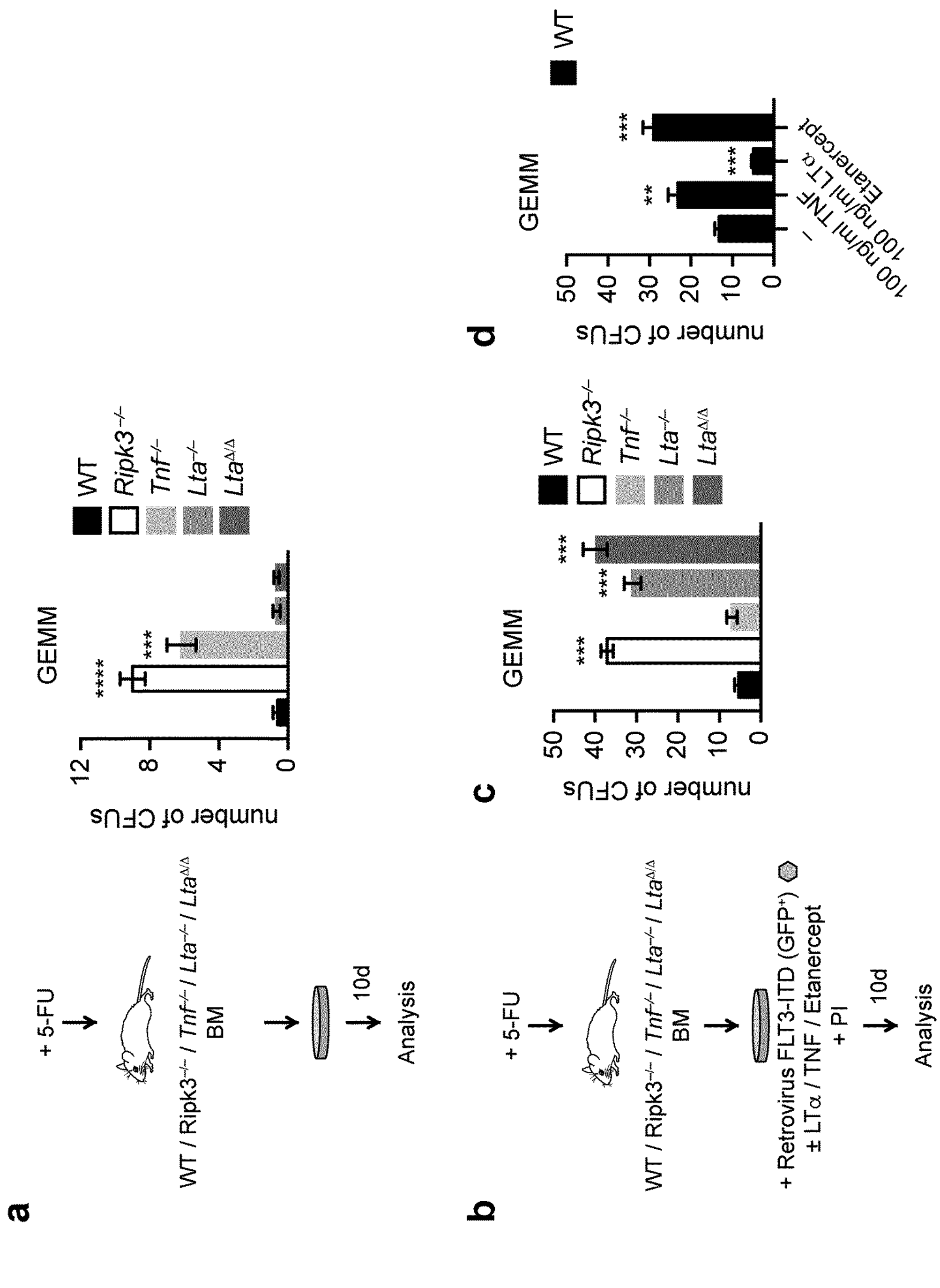
FIG. 2 shows that TNF signaling promotes the self-renewal of FLT3-ITD-mutated LSCs while LT-α restricts the same; (a) Experimental design and colony count of 5-FU-enriched HSPC. Shown are numbers of colony-forming units (CFU)—Granulocyte, Erythroid, Macrophage, Megakaryocyte (GEMM) (n=5 biological replicates for WT and $Lta^{\Delta/\Delta}$, n=4 for $Ripk3^{-/-}$, n=3 for $Lta^{-/-}$ and $Tnf^{-/-}$). Depicted p values were determined by comparison to WT. Data are representative of at least two independent experiments; (b) Experimental design; (c) GEMM colony count of FLT3-ITD-transduced BM (n=5 biological replicates for WT, n=4 for Ripk3$^{-/-}$ and LTa$^{\Delta/\Delta}$, n=3 for LTa$^{-/-}$ and Tnf$^{-/-}$). Data are representative of at least two independent experiments. Depicted p values were determined by comparison to WT; (d) GEMM colony count of FLT3-ITD-transduced BM treated as specified. (n=5 biological replicates). Data are representative of at least two independent experiments. Depicted p values were determined by comparison to control (–). Error bars represent mean±SEM. p values Student's t test. p<0.01, *p<0.001, ****p<0.0001.

TNF/LT-α blockade with the TNFR2-Ig fusion protein Etanercept in FLT3-ITD transduced cells, as expected, induced an increase in GEMM colonies in WT cultures compared to controls (FIG. 2*d*). This data supports the finding that LT-α is the ligand triggering the reduction in GEMM colonies.

Together, these data suggest that the FLT3-ITD oncogene skews TNFR signaling towards promoting HSPC self-renewal rather than suppressing it. In this oncogenic context, LT-α is the ligand capable of inducing cell death.

Administration of LT-α Eliminates AML In Vivo

The inventors further tested whether exogenous LT-α, an inhibitory antibody against TNF (a-TNF), or the combination thereof would be useful in treating leukemia. Since murine AML models have previously been used to predict the behavior of chemotherapy in the clinic, WT FLT3-ITD mice were generated and dosing 2- or 8-weeks post transplantation, respectively, was commenced (FIG. 3).

Figure 3:
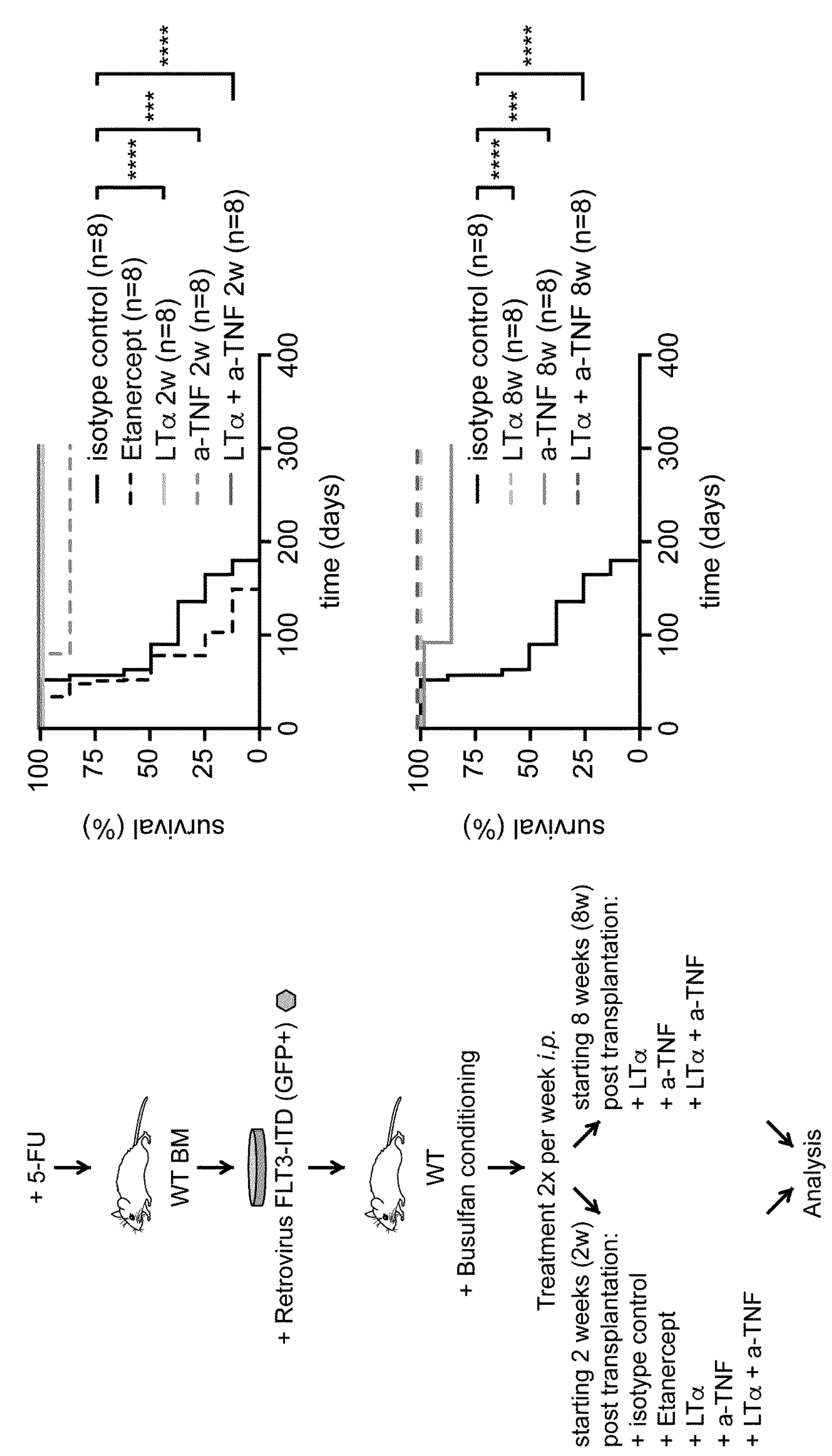
FIG. 3 shows that treatment of FLT3-ITD-transplanted mice with LT-α or a TNF-neutralizing antibody (a-TNF) eradicates LSCs, resulting in deep and durable remissions; Experimental design and survival of WT mice transplanted with FLT3-ITD-transduced WT BM, treated twice per week as specified. Median survival isotype control 76.5 days versus Etanercept 65 days. Number of mice as indicated in the figure. Error bars represent mean±SEM. p values Mantel-Cox test. *p<0.001, **p<0.0001.

LT-α and a-TNF treatment were well tolerated in vivo, reduced FLT3-ITD disease burden to <1% in all organs analysed, and induced durable remissions in treated animals, with survival extending 285 to 300 days after the treatment began (FIG. 3). Only 2 of the animals did not respond to a-TNF alone, whereas isotype control treated mice and those receiving Etanercept rapidly succumbed to disease (FIG. 3). Consistent with studies using HSPC-enriched BM, it was found that TNF/LT-α blockade with Etanercept drastically increased the number of primitive leukemic cells compared to controls, which was associated with a reduced latency, considerably elevated WBC counts, an increased hepatosplenomegaly, and an elevated leukemic burden (data not shown).

The combination treatment, LT-α+a-TNF, was as effective at reducing FLT3-ITD disease burden (<1%) and inducing durable remissions in WT FLT3-ITD mice as LT-α single treatment, however, addition of a-TNF did not accelerate leukemic cell death compared to LT-α single treatment. On the other hand, mice receiving the combination therapy gained weight faster compared to LT-α single treated animals (data not shown). This might indicate that treated mice experienced fatigue with rising LT-α concentration, for example by the onset of inflammatory processes, whereas simultaneous reduction of TNF improved fatigue over time.

Although we believe the depth and durability of responses seen here were primarily due to selective LSC targeting, the ability of these regimens to eradicate the bulk of leukemic cells, also in the periphery, is impressive.

In conclusion, LT-α (±a-TNF) is highly active in FLT3-ITD-AML; LSCs were effectively eradicated and remissions were deep and durable.

Figure 4:
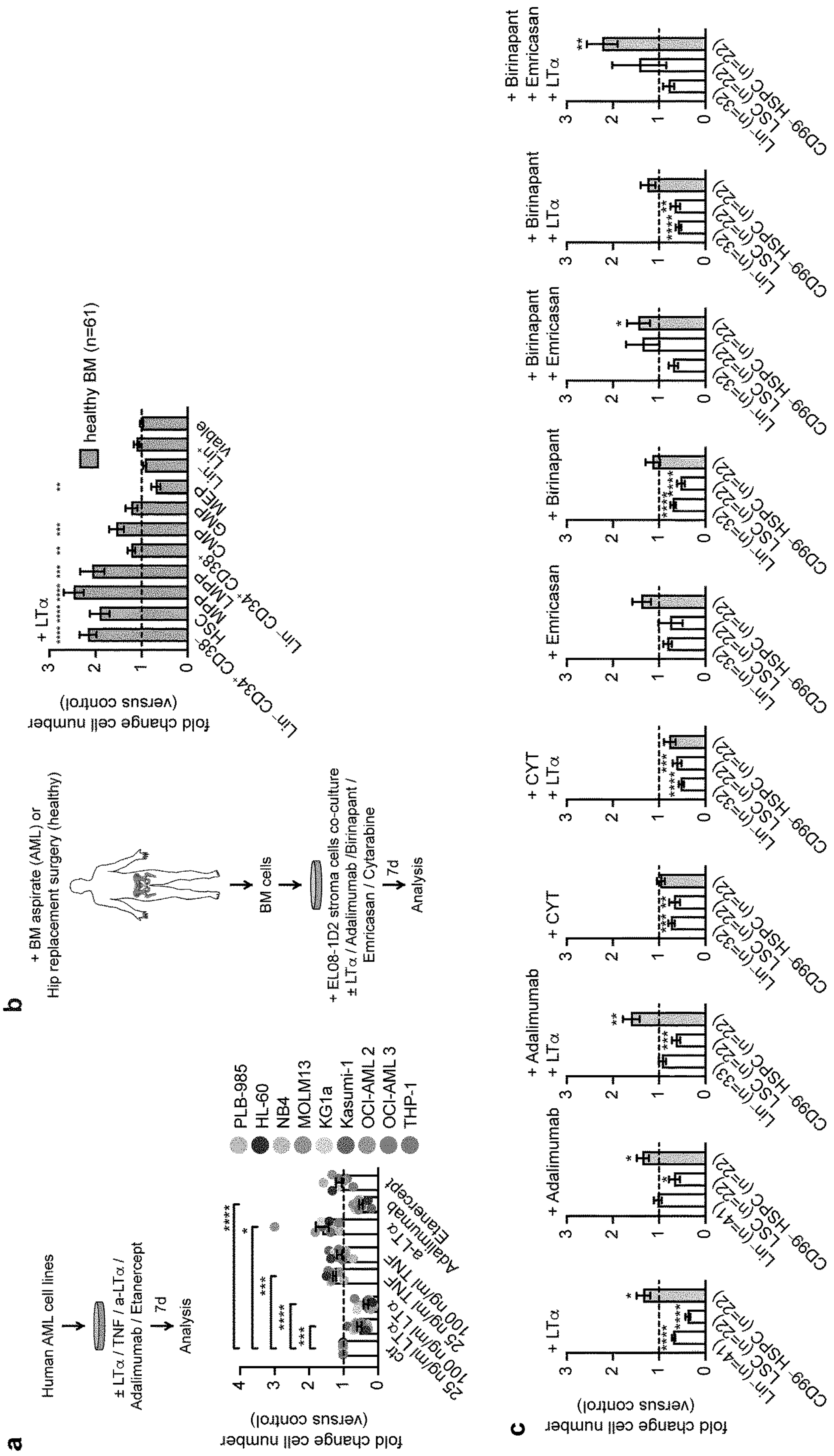
FIG. 4 shows that LT-α treatment kills LSCs and blast cells in a multitude of human primary AML samples, additive in combination with anti-TNF, cytarabine or IAP inhibition, but supports healthy HSPCs; (a) Relative number of cells in AML cell lines treated as specified (displayed as the mean of at least three technical repeats). Results are expressed as fold changes compared with untreated cells (ctr; set to 1, indicated by the dashed line); (b) Experimental design and relative number of hematopoietic cell subsets in healthy BM treated with 100 ng/ml LT-α. Results are expressed as fold changes compared with untreated cells (control; set to 1, indicated by the dashed line). Depicted p values were determined by comparison to control; (c) Relative number of Lin$^-$ cells, leukemic stem cells (LSC), and non-leukemogenic (CD99$^-$) HSPC in AML BM samples treated as specified (number of biological replicates per group as indicated in the figure). Results are expressed as fold changes compared with untreated cells (control; set to 1, indicated by the dashed line). Depicted p values were determined by comparison to control; Error bars represent mean±SEM. p values Student's t test. *p<0.05, p<0.01, *p<0.001, ****p<0.0001.

LT-α Combines with Cytarabine and Birinapant to Induce Cell Death in AML/Tolerability and Efficacy of LT-α Therapy were Evaluated in Human Primary Cells/LT-α is Efficient Against CML Alone as Well as in Combination with Imatinib To confirm that targeting TNFR signaling with LT-α/a-TNF is effective in the treatment of human AML, the inventors tested a panel of nine disparate AML cell line models for their sensitivity to LT-α/a-TNF (FIG. 4*a*). Indeed, exogenous LT-α specifically and significantly decreased the number of AML cells in a dose-dependent manner.

Accordingly, a drastic reduction in cell numbers upon blockade of TNF by the TNF specific antibody adalimumab could also be observed. In contrast, exogenous TNF or LT-α blockade with a LT-α neutralizing antibody significantly increased the number of AML cells. This effect, as expected, was not observed upon TNF/LT-α blockade with Etanercept (FIG. 4*a*). This indicated that, in agreement with our mouse model, the trophic activity of TNF and repression of LT-α were equally important for the survival and proliferation of AML cells. Importantly, the capacity to promote cell death by LT-α and TNF blockade was independent of the oncogenic mutations present in the cell lines.

To define the effects of exogenous LT-α on the healthy haematopoiesis the inventors treated bone marrow samples from healthy control patients and evaluated HSCs and myeloid progenitor subsets. Not only did LT-α not elicit any detectable toxic effect, but LT-α treatment sustained healthy haematopoiesis (FIG. 4*b*). Taken together, these data suggest that LT-α represents an intriguing approach for AML therapy.

To examine how targeting TNF/LT-α signaling can be most effectively used to treat AML, the inventors treated AML primary human samples in vitro. LT-α and a-TNF (Adalimumab) were evaluated, alone or in combination. Moreover, LT-α was tested in combination with the standard AML chemotherapeutic Cytarabine (CYT), the clinical SMAC mimetic Birinapant, and the clinical pan-caspase inhibitor Emricasan. Drug concentrations were determined after titration in healthy bone marrow samples and AML cell lines (data not shown). After 7-day-treatment, cell viability was evaluated, using CD99 to discriminate between non-leukaemogenic HSPCs ($CD99^{-}$) and LSCs (FIG. 4*c*).

LT α killed $Lin^{-}$ cells (containing the bulk of leukemia cells (AML blasts) and healthy HSPCs) and LSCs, while a-TNF killed only LSCs. Both LT-α and a-TNF promoted expansion of non-leukaemogenic HSPCs. Combination of Cytarabine or Birinapant with LT-α increased blast cell killing compared to Cytarabine or Birinapant single treatment. Birinapant was better at promoting cell death, both of blasts and LSCs, than Cytarabine. However, leukemic cells pretreated with Emricasan were resistant to LT-α- and Birinapant-induced cell death (FIG. 4*c*), demonstrating that LT-α/Birinapant induced also caspase-dependent cell death in several AML subtypes.

LT-α killed AML cells more effectively than the standard AML chemotherapeutic Cytarabine (ara-C) and even further increased cell death in combination with Cytarabine, without enhancing toxicity to healthy controls. Furthermore, LT-α is able to kill leukemic cells and leukemic stem cells in a more efficient manner than a-TNF, while LT-α is also able to support healthy hematopoiesis and lacks any pronounced cytotoxicity with regard to healthy cells.

In addition, experiments were carried out with the established, representative cell line for chronic myeloid leukemia K562. Based on the considerations above, it appeared plausible that the effect of LT-α may not be restricted to the individual disease AML but would rather extend to other myeloid diseases or neoplasms which originate from hematopoietic progenitor and stem cells.

Figure 5:
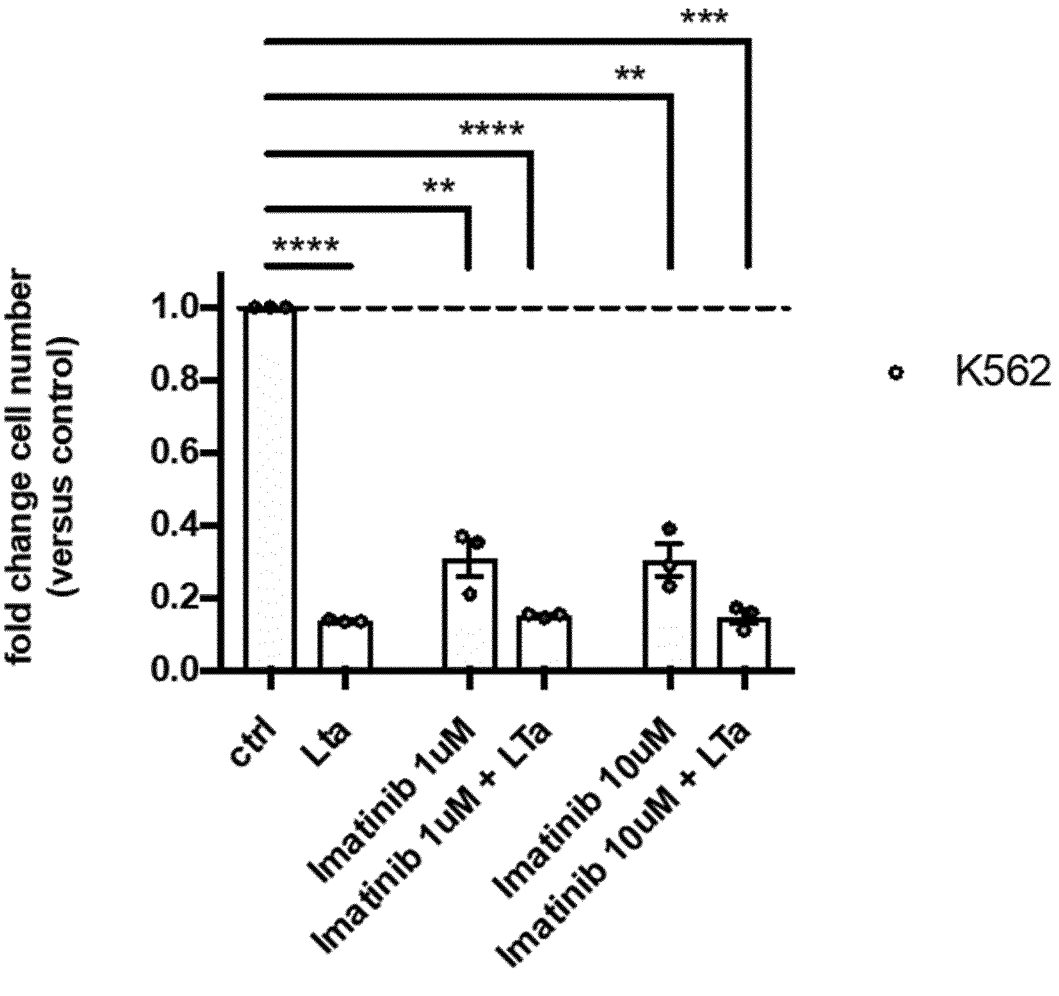
FIG. 5 shows that LT-α treatment kills blast cells of the representative chronic myeloid leukemia (CML) cell line K562, either individually or in combination with imatinib treatment. Relative number of cells treated as specified (displayed as the mean of three replicates). Results are expressed as fold changes compared with untreated cells (ctr; set to 1, indicated by the dashed line); Error bars represent mean±SEM. p values paired Student's t test. p<0.01, *p<0.001, ****p<0.0001.

As a model for CML, LT-α was tested for potential effects on the cell line K562, either separately against the standard therapy imatinib (in concentrations of 1 or 10 μM) alone, or in combination (FIG. 5). Based on the results obtained therewith, it could be demonstrated that LT-α has significant effects alone as well as in combination with the standard therapy imatinib. Thus, LT-α could potentially further be used as a stand-alone therapy or in combination to complement the effects of imatinib to treat CML.

The results observed with CML as a different type of myeloid disease having a different clinical picture than AML, but also originating from HSPCs and potentially connected to a role of LSCs in the disease, suggest a general applicability of the claimed therapy for a wide variety of myeloid diseases and neoplasms.

Based on these properties, LT-α is a promising candidate for a highly advantageous method of treating patients suffering from myeloid diseases or myeloid neoplasms, such as AML, CML or others in comparison to the currently available methods of treatment.

The invention claimed is:

1. A method of treating Acute Myeloid Leukemia (AML) comprising administering to a patient in need thereof an effective amount of a polypeptide comprising the amino acid sequence of SEQ ID No. 1 (full length human Lymphotoxin-alpha (LT-α) or of SEQ ID No. 2 (recombinant mature form of human LT-α with N-terminal methionine) or comprising an amino acid sequence having at least 90% identity to the amino acid sequence of SEQ ID No. 1 or SEQ ID No. 2.

2. The method according to claim 1, wherein the polypeptide affects a Tumor Necrosis Factor Receptor Superfamily (TNFRSF)-dependent signal cascade.

3. The method according to claim 2, wherein the signaling pathway affected by the polypeptide is fully or partially functional in the patient to be treated.

4. The method according to claim 2, wherein the polypeptide affects TNFR1, TNFR2, lymphotoxin beta receptor or HVEM.

5. The method according to claim 1, wherein the polypeptide induces programmed cell death.

6. The method according to claim 5, wherein the polypeptide induces programmed cell death exclusively in one or more of leukemia cells, leukemic progenitor cells, and leukemic stem cells.

7. The method according to claim 1, wherein the polypeptide is a recombinant polypeptide or a purified endogenous polypeptide.

8. The method according to claim 1, wherein the patient is human.

9. The method according to claim 1, wherein the polypeptide consists of the amino acid sequence of SEQ ID No. 1 or of SEQ ID No. 2 or of an amino acid sequence having at least 90% identity to the amino acid sequence of SEQ ID No. 1 or of SEQ ID No. 2.

10. The method according to claim 9, wherein the polypeptide consists of the amino acid sequence of SEQ ID No. 2.

11. The method according to claim 1, wherein the polypeptide is administered to the patient by way of systemic administration.

12. The method according to claim 11, wherein the pharmaceutical composition is administered to the patient by way of intravenous administration or subcutaneous administration.

13. A pharmaceutical composition formulated for treating Acute Myeloid Leukemia (AML) comprising a polypeptide comprising the amino acid sequence of SEQ ID No. 1 (full length human Lymphotoxin-alpha (LT-α)) or of SEQ ID No. 2 (native mature form of human LT-α) or comprising an amino acid sequence having at least 90% identity to the amino acid sequence of SEQ ID No. 1 or SEQ ID No. 2, wherein the pharmaceutical composition further comprises one or more substances selected from a Second Mitochondria-derived Activator of Caspases (SMAC) mimetic, a chemotherapy agent or a TNF inhibitor.

14. The pharmaceutical composition according to claim 13, wherein the pharmaceutical composition does not comprise any type of Tumor Necrosis Factor (TNF) receptor molecule including the Tumor Necrosis Factor Receptor 1 (TNFR1) (SEQ ID No. 3), Tumor Necrosis Factor Receptor 2 (TNFR2) (SEQ ID No. 4), lymphotoxin beta receptor (SEQ ID No. 5), Herpesvirus Entry Mediator (HVEM) (SEQ ID No. 6), or antibodies directed against lymphotoxin or against any type of TNF receptor including the TNFR1, TNFR2, lymphotoxin beta receptor, and HVEM.

15. The pharmaceutical composition according to claim 13, wherein the SMAC mimetic comprises birinapant, the chemotherapy agent comprises cytosine arabinoside or daunorubicine and the TNF inhibitor comprises adalimumab, infliximab, golimumab, or certolizumab pegol.

16. A kit comprising a polypeptide and a container, wherein the polypeptide comprises the amino acid sequence of SEQ ID No. 1 (full length human Lymphotoxin-alpha (LT-α)) or of SEQ ID No. 2 (native mature form of human LT-α) or the polypeptide comprises an amino acid sequence having at least 90% identity to the amino acid sequence of SEQ ID No. 1 or SEQ ID No. 2, wherein the kit further comprises one or more substances for combination with the polypeptide selected from a Second Mitochondria-derived Activator of Caspases (SMAC) mimetic, a chemotherapy agent or a TNF inhibitor, wherein the polypeptide is formulated for treating Acute Myeloid Leukemia (AML).

* * * * *